(12) United States Patent
Al Wakeel

(10) Patent No.: US 9,861,734 B2
(45) Date of Patent: Jan. 9, 2018

(54) BIFURCATED PERITONEAL CATHETER

(71) Applicant: KING SAUD UNIVERSITY, Riyadh (SA)

(72) Inventor: Jamal S. Al Wakeel, Riyahd (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 15/076,614

(22) Filed: Mar. 21, 2016

(65) Prior Publication Data

US 2017/0266361 A1    Sep. 21, 2017

(51) Int. Cl.
*A61M 1/28*    (2006.01)

(52) U.S. Cl.
CPC .................... *A61M 1/285* (2013.01)

(58) Field of Classification Search
CPC .............. A61M 1/3661; A61M 25/007; A61M 25/0041; A61M 2210/1017
USPC .............................................. 604/29, 43, 264
See application file for complete search history.

(56) References Cited

U.S. PATENT DOCUMENTS

| | | | | |
|---|---|---|---|---|
| 4,681,564 A * | 7/1987 | Landreneau | ...... | A61M 25/1002 604/128 |
| 4,738,667 A * | 4/1988 | Galloway | .............. | A61M 25/04 604/530 |
| 5,156,592 A | 10/1992 | Martin et al. | | |
| 5,254,084 A * | 10/1993 | Geary | .................... | A61M 1/285 604/29 |
| 5,322,521 A * | 6/1994 | Wilk | ..................... | A61M 1/008 433/91 |
| 5,599,304 A * | 2/1997 | Shaari | .................... | A61M 1/008 604/173 |
| 5,873,865 A * | 2/1999 | Horzewski | ........ | A61M 25/0041 604/523 |
| 5,947,953 A | 9/1999 | Ash et al. | | |
| 6,245,039 B1 * | 6/2001 | Brugger | ................ | A61M 1/285 604/29 |
| 6,402,736 B1 * | 6/2002 | Brown | .............. | A61M 25/0017 604/264 |
| 6,592,542 B2 * | 7/2003 | Childers | ................. | A61M 1/28 604/29 |
| 6,758,836 B2 * | 7/2004 | Zawacki | ............. | A61M 1/3653 604/284 |
| 6,911,014 B2 * | 6/2005 | Wentling | ............. | A61M 1/285 604/284 |
| 6,921,396 B1 * | 7/2005 | Wilson | ............. | A61M 25/0069 604/508 |

(Continued)

OTHER PUBLICATIONS

Website, www.medcompnet.com, "X-Series Peritoneal Dialysis Catheters," printed from the internet on Dec. 13, 2015.

*Primary Examiner* — Gerald Landry, II
(74) *Attorney, Agent, or Firm* — Richard C. Litman

(57) ABSTRACT

The bifurcated peritoneal catheter serves as a peritoneal dialysis device for patients with kidney failure. The catheter includes a primary tube with two porous internal tubes extending therefrom at a small acute angle to one another. The two internal tubes provide a solution to the potential problem of blockage in a single catheter tube, greatly reducing the potential need for surgery to remove and replace such a single catheter tube. The bifurcated peritoneal catheter includes a subcutaneous cuff, and can include a second deep cuff in the abdominal wall. Either or both of the internal tubes can be straight, curved or coiled, with the curvatures and coils oriented in the same direction, toward one another, or away from one another.

1 Claim, 13 Drawing Sheets

(56) References Cited

U.S. PATENT DOCUMENTS

| | | | |
|---|---|---|---|
| 6,976,973 B1* | 12/2005 | Ruddell | A61M 1/284 604/264 |
| 7,276,043 B2* | 10/2007 | Heath | A61M 25/0023 604/43 |
| 7,320,674 B2 | 1/2008 | Ruddell et al. | |
| 7,393,339 B2* | 7/2008 | Zawacki | A61M 25/0026 604/43 |
| 8,282,623 B2* | 10/2012 | Klein | A61F 5/003 604/540 |
| 9,168,355 B2 | 10/2015 | Braga | |
| 2002/0091362 A1 | 7/2002 | Maginot et al. | |
| 2002/0188167 A1* | 12/2002 | Viole | A61M 1/3653 600/16 |
| 2003/0069534 A1* | 4/2003 | Work | A61M 1/285 604/43 |
| 2004/0193098 A1* | 9/2004 | Wentling | A61M 1/285 604/29 |
| 2005/0131340 A1* | 6/2005 | Sorenson | A61M 1/28 604/29 |
| 2005/0209579 A1* | 9/2005 | Yacoubian | A61M 25/0069 604/500 |
| 2006/0155250 A1* | 7/2006 | Endo | A61M 1/285 604/264 |
| 2009/0018493 A1* | 1/2009 | Ash | A61M 1/284 604/29 |
| 2009/0209940 A1* | 8/2009 | Nimkar | A61M 25/001 604/523 |
| 2013/0281761 A1* | 10/2013 | Kapur | A61M 1/3659 600/17 |
| 2014/0031742 A1* | 1/2014 | Kim | A61B 17/42 604/35 |
| 2014/0330220 A1 | 11/2014 | Zawacki et al. | |
| 2015/0306302 A1 | 10/2015 | Marsden et al. | |

\* cited by examiner

BIFURCATED PERITONEAL CATHETER

BACKGROUND OF THE INVENTION

1. Field of the Invention

The present invention relates generally to medical and surgical appliances and devices, and particularly to a series of embodiments of a bifurcated peritoneal catheter.

2. Description of the Related Art

Kidney failure, and particularly end stage renal failure, is an ultimately fatal disease that affects millions of people. The result is a buildup of impurities within the peritoneal cavity of the body. These impurities cannot be eliminated by the body, at least not to the degree necessary to maintain health. The only known cures at present are (1) peritoneal dialysis to purge waste materials from the body, or (2) kidney transplant from a suitable donor, which procedure is beyond the scope of the present invention.

In the case of peritoneal dialysis, a single tubular catheter (generally known as a Tenckhoff catheter, after its developer) is surgically installed within the peritoneal cavity of the patient. The catheter is used to periodically infuse a dialysate fluid into the peritoneal cavity, with the dialysate becoming contaminated with the collected impurities within the peritoneal cavity. The contaminated dialysate is then drawn from the patient's body. This procedure is normally performed a few times per day to maintain the health of the patient.

There are a number of potential problems that can occur with peritoneal catheters. For example, the single tube of the catheter can become displaced from the pelvic area, or perhaps become blocked due to fibrin buildup, or the open distal end can come in contact with some internal organ (bowel, etc.) to reduce fluid flow through the catheter. These problems have a frequency of occurrence approaching twenty percent. The only recourse is the surgical removal of the peritoneal catheter, repositioning of the catheter, or reinstallation of a new catheter.

Thus, a bifurcated peritoneal catheter solving the aforementioned problems is desired.

SUMMARY OF THE INVENTION

The bifurcated peritoneal catheter comprises a single primary tube having the majority of its length disposed externally to the body. A subcutaneous cuff seals the tube at its entrance into the body. A deeper second cuff at the abdominal wall can also be provided. Two internal catheter tubes connect to the distal end of the primary tube at a small acute angle, to provide minimal turbulence to internal fluid flow at the juncture of the internal tubes with the distal end of the primary tube. Fluid flow through the tubes is always in the same direction, i.e., the two internal tubes (as well as the primary tube, of course) simultaneously provide inflow of dialysate or outflow of contaminated fluid. The two internal tubes provide alternative flow paths in the event that one of the internal tubes becomes blocked, thereby greatly reducing the need for a subsequent operation to remove the catheter assembly and reinstall another.

A number of different embodiments are disclosed herein. The primary tube can have a single or double cuff, as noted further above. The distal end of the primary tube, i.e., that portion within the body, can be straight or can have a curve, known as a "swan neck," particularly between the two cuffs when two such cuffs are provided. The two internal tubes can be straight, or either or both can be curved. Either or both of the internal tubes can be coiled, with the coil(s) oriented toward or away from the other internal tube. The tubes are devoid of internal structure and remain in their natural straight, curved, or coiled configurations after surgical implantation.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The bifurcated peritoneal catheter provides a second internal catheter tube, i.e., within the peritoneal cavity of the patient, to provide a secondary or backup path for the introduction of dialysate fluid and the withdrawal of contaminated fluid during peritoneal dialysis. This greatly reduces the need for surgery to remove a single internal tube and to install a new tube in the patient, as there is a much greater likelihood that one of the two internal tubes will remain open. As both internal tubes perform the same function, fluid flow through the two internal tubes and the primary tube is always in the same direction at any given time, i.e., into the peritoneal cavity or out from the peritoneal cavity. A number of different embodiments are disclosed herein.

Figure 1:
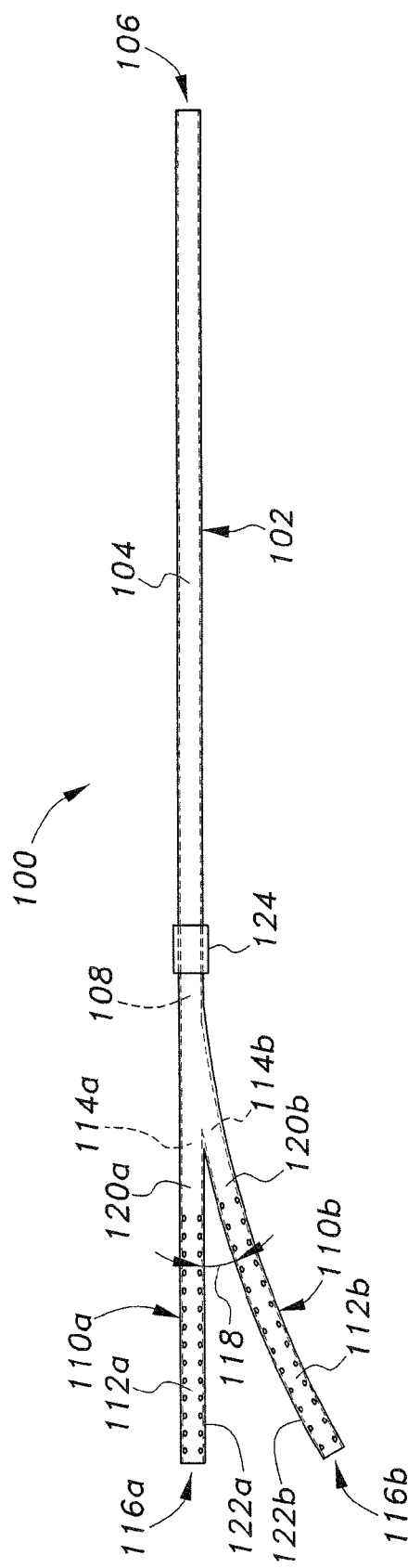
FIG. 1 is a top plan view of a first embodiment of a bifurcated peritoneal catheter according to the present invention, wherein a single subcutaneous cuff is disposed along the entry tube and one leg of the catheter is straight.

FIG. 1 of the drawings illustrates a top plan view of a first embodiment of the bifurcated peritoneal catheter, designated as bifurcated peritoneal catheter (or catheter) 100. The catheter 100 includes a thin, elongate primary tube 102 having a closed wall 104 with an open proximal end 106 and an opposite open distal end 108. Some portion of the length of the primary tube 102 to the proximal end 106 thereof extends externally from the patient to appropriate fluid delivery and collection points external to the patient during the dialysis procedure. The distal end portion 108 of the primary tube 102 is surgically implanted within the patient.

First and second internal tubes, respectively 110a and 110b, are adapted for surgical placement within the peritoneal cavity of the patient. Each of these two internal tubes 110a, 110b comprise a long, thin element having a wall, respectively 112a and 112b, with an open proximal end, respectively 114a and 114b, and opposite open distal end, respectively 116a and 116b. The proximal ends 114a, 114b of the two internal tubes 110a, 110b are joined to and communicate with the distal end 108 of the primary tube 102 and with one another and foil a small acute angle 118 between the two proximal ends 114a, 114b, e.g., on the order of twenty to thirty degrees included angle therebetween. This greatly improves the fluid flow through the bifurcated catheter 100 by reducing fluid turbulence at the juncture of the tubes. It will be seen that this structure results in unidirectional flow of any fluid flowing within the catheter 100 at any given time, as fluid cannot flow in one direction through one of the internal tubes and in an opposite direction in the other of the internal tubes due to their common connection to and communication with the distal end 108 of the primary tube 102. The walls 112a, 112b of the two internal tubes 110a, 110b have closed portions 120a, 120b extending for some lengths from points adjacent their proximal ends 114a, 114b, but have porous portions 122a, 122b extending for some lengths from points adjacent their distal ends 116a, 116b to the closed wall portions 120a, 120b thereof.

In the catheter 100 example of FIG. 1, a single annular subcutaneous cuff 124 is located concentrically about the distal end 108 of the primary tube 102, adjacent its juncture with the proximal ends 114a and 114b of the two internal tubes 110a and 110b. This subcutaneous cuff 124 serves as a seal between the skin and body of the patient and the primary tube 102. An additional cuff may be provided, as shown and described further below for other embodiments. It will also be noted in the catheter 100 example of FIG. 1 that the first internal tube 110a is substantially straight, while the second internal tube 110b is curved away from the first internal tube 110a. This configuration is exemplary and any practicable number of different straight, curved, and/or coiled internal tubes can be formed, with various examples illustrated in subsequent drawing Figs. and described below.

Figure 2:
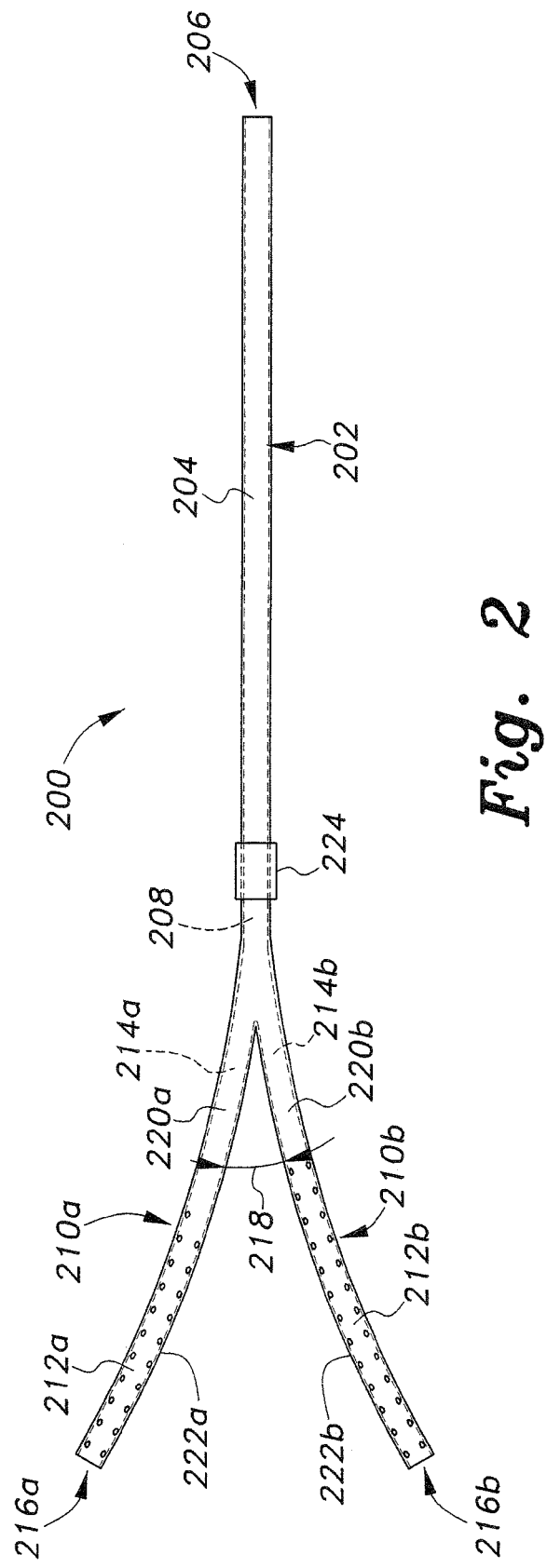
FIG. 2 is a top plan view of a second embodiment of the bifurcated peritoneal catheter according to the present invention, wherein a single subcutaneous cuff is disposed along the entry tube and both catheter legs are slightly curved.

FIG. 2 of the drawings illustrates a second embodiment bifurcated peritoneal catheter 200. The catheter 200 is configured similarly to the catheter 100 of FIG. 1, i.e., having a thin, elongate primary tube 202 with a closed wall 204, open proximal end 206, and opposite open distal end 208. It will be seen that the length of the primary tube 202 is somewhat shorter than the length of the primary tube 102 of the catheter 100 of FIG. 1. The primary tube lengths of any of the bifurcated peritoneal catheters described herein, as well as their two internal catheters, can be formed or adjusted as desired.

First and second internal tubes, respectively 210a and 210b, are also adapted for surgical placement within the peritoneal cavity of the patient. These two internal tubes 210a, 210b each comprise a long, thin element having a wall, respectively 212a and 212b, with an open proximal end, respectively 214a and 214b, and opposite open distal end, respectively 216a and 216b. The proximal ends 214a, 214b of the two internal tubes 210a, 210b are joined to and communicate with the distal end 208 of the primary tube 202 and with one another and form a small acute angle 218 between the two proximal ends 214a, 214b, e.g., on the order of twenty to thirty degrees included angle therebetween. The walls 212a, 212b of the two internal tubes 210a, 210b have closed portions 220a, 220b extending for some lengths from points adjacent their proximal ends 214a, 214b, but have porous portions 222a, 222b extending for some lengths from points adjacent their distal ends 216a, 216b to the closed wall portions 220a, 220b thereof. A single annular subcutaneous cuff 224 is located concentrically about the distal end 208 of the primary tube 202, adjacent its juncture with the proximal ends 214a and 214b of the two internal tubes 210a and 210b.

It will be noted in the catheter 200 example of FIG. 2 that both of the internal tubes 210a and 210b are curved away from one another. This, and the shorter length of the primary tube 202, is the primary distinction between the bifurcated peritoneal catheter embodiment 100 of FIG. 1 and the embodiment 200 of FIG. 2.

Figure 3:
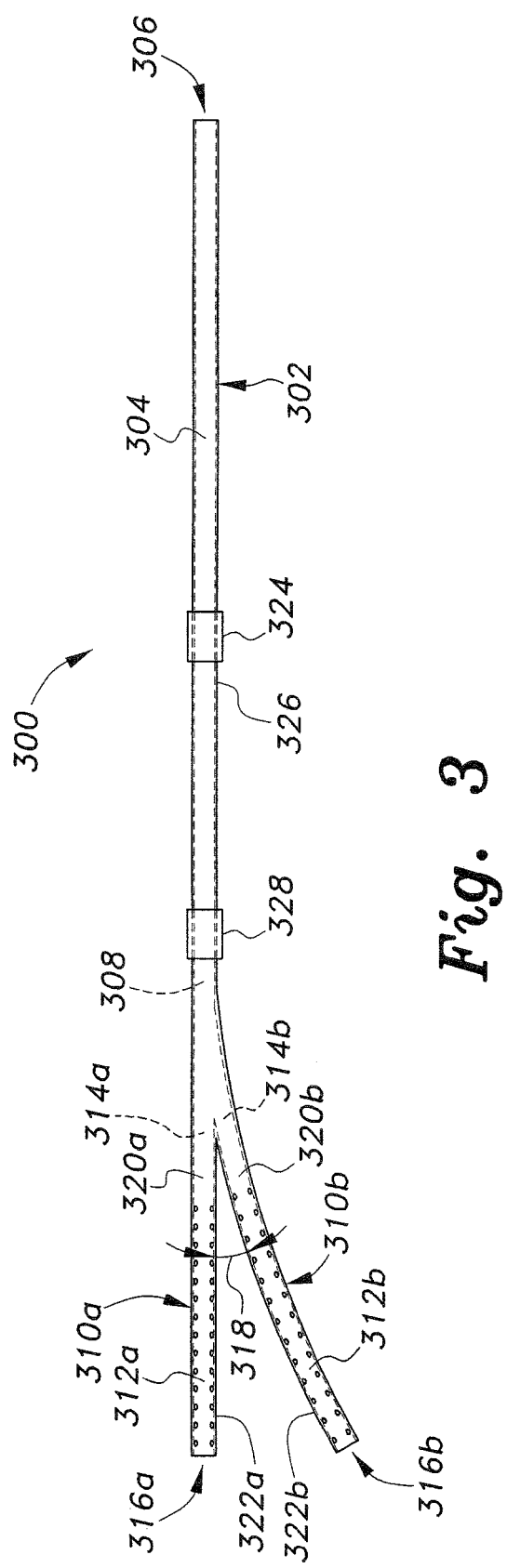
FIG. 3 is a top plan view of a third embodiment of the bifurcated peritoneal catheter according to the present invention, wherein subcutaneous and abdominal muscle wall cuffs are provided along the entry tube of the bifurcated peritoneal catheter embodiment of FIG. 1.

FIG. 3 of the drawings illustrates a third embodiment 300 of the bifurcated peritoneal catheter. The catheter 300 is configured similarly to the catheter 100 of FIG. 1, i.e., having a thin, elongate primary tube 302 with a closed wall 304, open proximal end 306, and opposite open distal end 308. First and second internal tubes, respectively 310a and 310b, extend from the distal end 308 of the primary tube 302, with the first and second internal tubes each comprising a long, thin element having a wall, respectively 312a and 312b, an open proximal end, respectively 314a and 314b, and opposite open distal end, respectively 316a and 316b. The proximal ends 314a, 314b of the two internal tubes 310a, 310b are joined to and communicate with the distal end 308 of the primary tube 302 and with one another and form a small acute angle 318 between the two proximal ends 314a, 314b, e.g., on the order of twenty to thirty degrees included angle therebetween. The walls 312a, 312b of the two internal tubes 310a, 310b have closed portions 320a, 320b extending for some lengths from points adjacent their proximal ends 314a, 314b, but have porous portions 322a, 322b extending for some lengths from points adjacent their distal ends 316a, 316b to the closed wall portions 320a, 320b thereof. The first internal tube 310a is straight and the second internal tube 310b is curved, as in the bifurcated peritoneal catheter embodiment 100 of FIG. 1.

The above-described structure of the third embodiment catheter 300 is essentially the same as that of the first embodiment catheter 100 of FIG. 1. However, it will be seen that the bifurcated peritoneal catheter 300 of FIG. 3 includes two annular cuffs thereon. A first annular cuff 324 comprising a subcutaneous cuff is located about the medial portion 326 of the primary tube 302, with a second or deep cuff 328 disposed about the distal end 308 of the primary tube 302 adjacent its juncture with the proximal ends 314a and 314b of the two internal tubes 310a and 310b. The second or deep cuff 328 provides a secure passage for the distal end 308 of the primary tube 302 through the abdominal wall of the patient.

Figure 4:
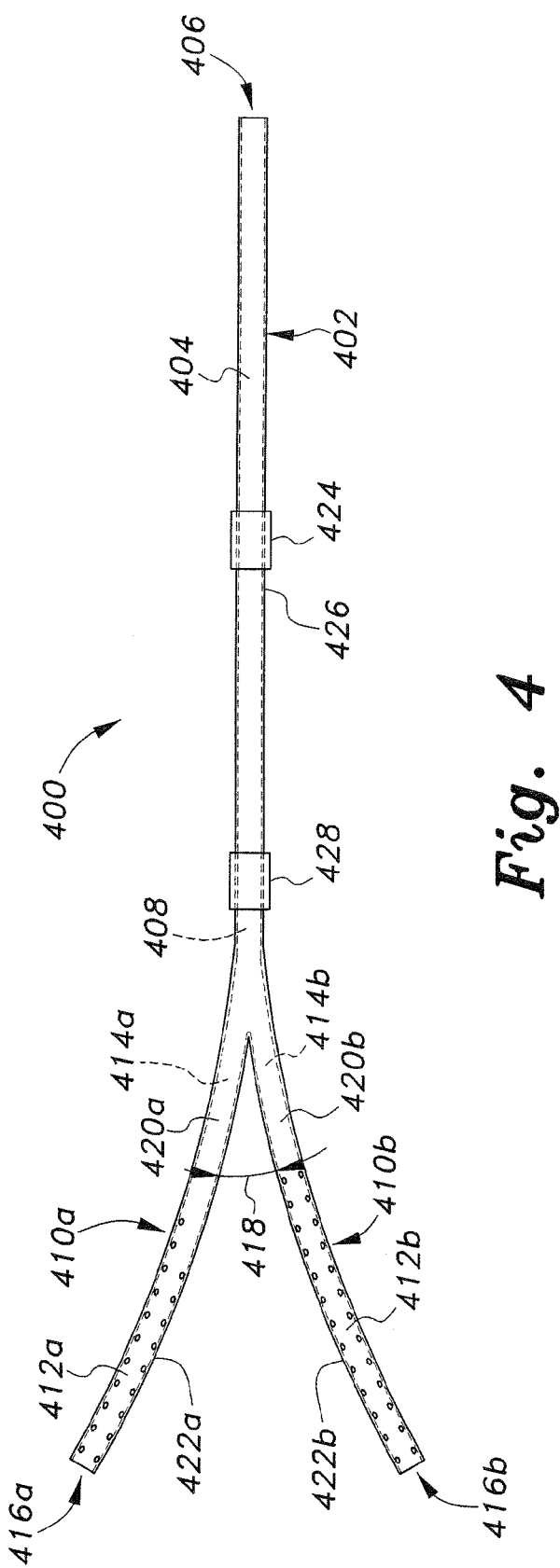
FIG. 4 is a top plan view of a fourth embodiment of the bifurcated peritoneal catheter according to the present invention, wherein subcutaneous and abdominal muscle wall cuffs are provided along the entry tube of the bifurcated peritoneal catheter embodiment of FIG. 2.

FIG. 4 of the drawings illustrates a fourth embodiment 400 of the bifurcated peritoneal catheter. The catheter 400 is configured similarly to the catheter 300 of FIG. 3, i.e., having a thin, elongate primary tube 402 with a closed wall 404, open proximal end 406, and opposite open distal end 408. First and second internal tubes, respectively 410a and 410b, extend from the distal end 408 of the primary tube 402, with the first and second internal tubes each comprising a long, thin element having a wall, respectively 412a and 412b, an open proximal end, respectively 414a and 414b, and opposite open distal end, respectively 416a and 416b. The proximal ends 414a, 414b of the two internal tubes 410a, 410b are joined to and communicate with the distal end 408 of the primary tube 402 and with one another and form a small acute angle 418 between the two proximal ends 414a, 414b, e.g., on the order of twenty to thirty degrees included angle therebetween. The walls 412a, 412b of the two internal tubes 410a, 410b have closed portions 420a, 420b extending for some lengths from points adjacent their proximal ends 414a, 414b, but have porous portions 422a, 422b extending for some lengths from points adjacent their distal ends 416a, 416b to the closed wall portions 420a, 420b thereof. The bifurcated peritoneal catheter embodiment 400 of FIG. 4 differs from the embodiment 300 of FIG. 3 in that both of the two internal tubes 410a, 410b have slight curvatures and are curved away from each other, as in the catheter embodiment 200 of FIG. 2.

The above-described structure of the fourth embodiment catheter 400 is essentially the same as that of the first embodiment catheter 200 of FIG. 2. However, it will be seen that the bifurcated peritoneal catheter 400 of FIG. 4 includes two annular cuffs thereon. A first annular cuff 424 comprising a subcutaneous cuff is located about the medial portion 426 of the primary tube 402, with a second or deep cuff 428 disposed about the distal end 408 of the primary tube 402 adjacent its juncture with the proximal ends 414a and 414b of the two internal tubes 410a and 410b.

Figure 5:
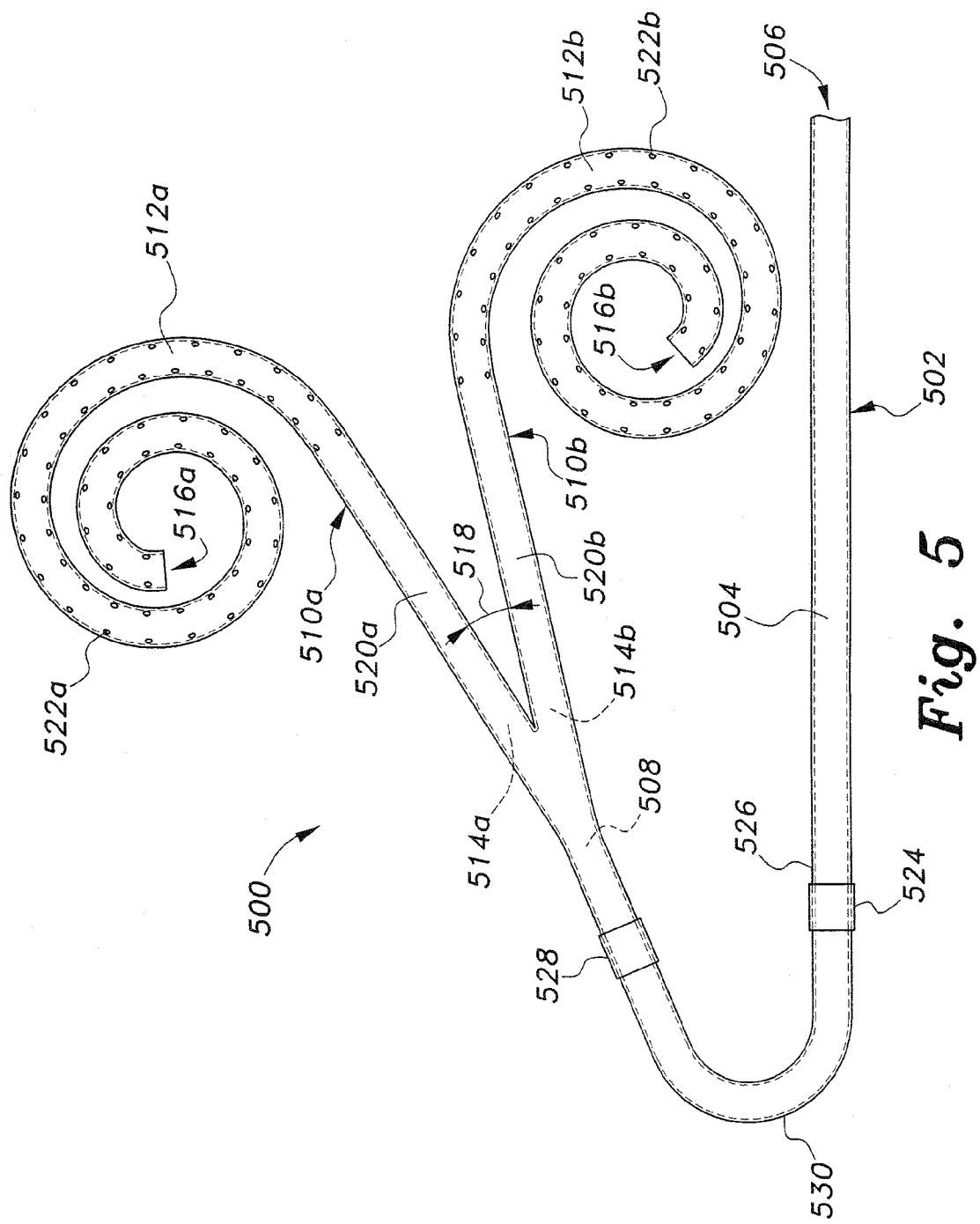
FIG. 5 is a top plan view of a fifth embodiment of the bifurcated peritoneal catheter according to the present invention, wherein the entry tube includes an acute bend between the two cuffs and the two peritoneal tubes are coiled away from one another.

FIG. 5 of the drawings illustrates a fifth embodiment 500 of the bifurcated peritoneal catheter. The components of the catheter 500 are somewhat analogous to those of the catheter 400 of FIG. 4, i.e., having a thin, elongate primary tube 502 with a closed wall 504, open proximal end 506, and opposite open distal end 508. First and second internal tubes, respectively 510a and 510b, extend from the distal end 508 of the primary tube 502, with the first and second internal tubes each comprising a long, thin element having a wall, respectively 512a and 512b, an open proximal end, respectively 514a and 514b, and opposite open distal end, respectively 516a and 516b. The proximal ends 514a, 514b of the two internal tubes 510a, 510b are joined to and communicate with the distal end 508 of the primary tube 502 and with one another and form a small acute angle 518 between the two proximal ends 514a, 514b, e.g., on the order of twenty to thirty degrees included angle therebetween. The walls 512a, 512b of the two internal tubes 510a, 510b have closed portions 520a, 520b extending for some lengths from points adjacent their proximal ends 514a, 514b, but have porous portions 522a, 522b extending for some lengths from points adjacent their distal ends 516a, 516b to the closed wall portions 520a, 520b thereof. The bifurcated peritoneal catheter 500 of FIG. 5 includes two annular cuffs thereon, as in the catheter embodiments 300 of FIG. 3 and 400 of FIG. 4. A first annular cuff 524 comprising a subcutaneous cuff is located about the medial portion 526 of the primary tube 502, with a second or deep cuff 528 disposed about the distal end 508 of the primary tube 502 adjacent its juncture with the proximal ends 514a and 514b of the two internal tubes 510a and 510b.

The bifurcated peritoneal catheter embodiment 500 of FIG. 5 differs from the embodiment 400 of FIG. 4 in two different ways related to the orientation of the primary tube 502 and the two internal tubes 510a and 510b. First, it will be seen that the primary tube 502 includes an acute bend or curvature 530 between the two cuffs 524 and 528. (This is known as a "swan neck" curve in the field of the invention.) This assists in positioning the external portion of the primary tube 502 relative to the patient. Second, it will be seen that both of the porous wall portions 522a and 522b of the two internal tubes 510a, 510b are coiled, with the coiled portions subtending approximately 570 degrees, more or less. This provides a greater length of internal tube in a relatively small area, in order to more efficiently distribute dialysate fluid and draw contaminated fluid from the peritoneal cavity of the patient. In the example of FIG. 5, the first coiled portion 522a is coiled in a first direction, e.g., counterclockwise in the plan view of FIG. 5, with the second coiled portion 522b being coiled opposite the direction of the first coiled portion 522a, i.e., clockwise for the second coiled portion.

Figure 6:
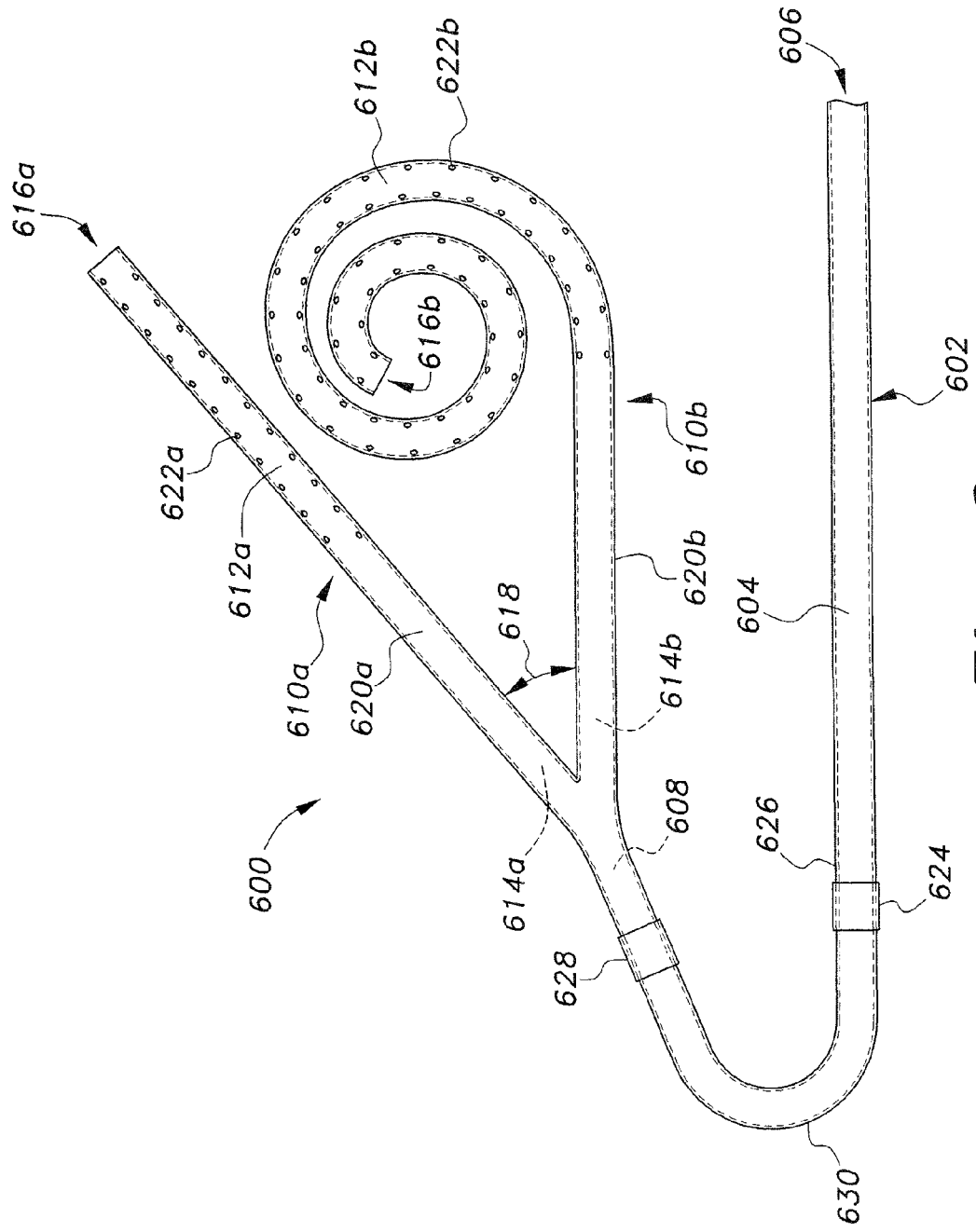
FIG. 6 is a top plan view of a sixth embodiment of the bifurcated peritoneal catheter according to the present invention, wherein the entry tube includes an acute bend between the two cuffs and one of the two peritoneal tubes is coiled toward the other.

FIG. 6 of the drawings illustrates a sixth embodiment 600 of the bifurcated peritoneal catheter. The components of the catheter 600 are somewhat analogous to those of the catheter 500 of FIG. 5, i.e., having a thin, elongate primary tube 602 with a closed wall 604, open proximal end 606, and opposite open distal end 608. First and second internal tubes, respectively 610a and 610b, extend from the distal end 608 of the primary tube 602, with the first and second internal tubes each comprising a long, thin element having a wall, respectively 612a and 612b, an open proximal end, respectively 614a and 614b, and opposite open distal end, respectively 616a and 616b. The proximal ends 614a, 614b of the two internal tubes 610a, 610b are joined to and communicate with the distal end 608 of the primary tube 602 and with one another and form a small acute angle 618 between the two proximal ends 614a, 614b, e.g., on the order of twenty to thirty degrees included angle therebetween. The walls 612a, 612b of the two internal tubes 610a, 610b have closed portions 620a, 620b extending for some lengths from points adjacent their proximal ends 614a, 614b, but have porous portions 622a, 622b extending for some lengths from points adjacent their distal ends 616a, 616b to the closed wall portions 620a, 620b thereof. The bifurcated peritoneal catheter 600 of FIG. 6 includes two annular cuffs thereon, as in the catheter embodiments 300, 400, and 500, respectively of FIGS. 3, 4, and FIG. 5. A first annular cuff 624 comprising a subcutaneous cuff is located about the medial portion 626 of the primary tube 602, with a second or deep cuff 628 disposed about the distal end 608 of the primary tube 602 adjacent its juncture with the proximal ends 614a and 614b of the two internal tubes 610a and 610b.

The bifurcated peritoneal catheter embodiment 600 of FIG. 6 differs from the embodiment 500 of FIG. 5 due to the configurations of the internal tubes 610a and 610b. It will be seen that the first internal tube 610a is straight, while the porous wall portion 612b of the second internal tube 610b is coiled, with the coiled portion subtending approximately 570 degrees, more or less. In the example of FIG. 6, the coiled portion 622b of the second internal tube 610b is coiled in a first direction, e.g., counterclockwise in the plan view of FIG. 6, resulting in its coil being toward the straight length of the first internal tube 610a.

Figure 7:
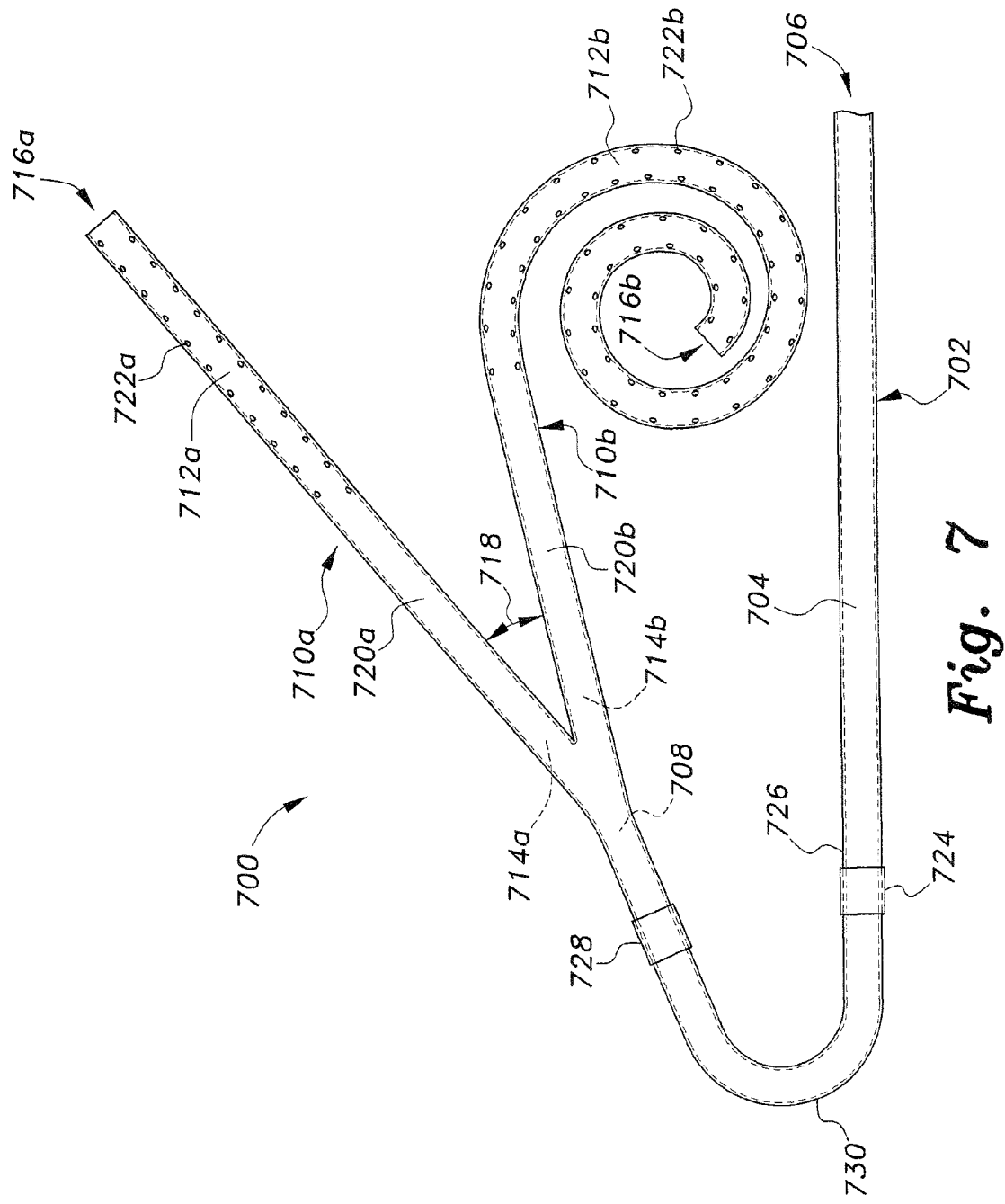
FIG. 7 is a top plan view of a seventh embodiment of the bifurcated peritoneal catheter according to the present invention, wherein the entry tube includes an acute bend between the two cuffs and one of the two peritoneal tubes is coiled away from the other.

FIG. 7 of the drawings illustrates a sixth embodiment 700 of the bifurcated peritoneal catheter. The components of the catheter 700 are essentially similar to those of the catheter 600 of FIG. 6, i.e., having a thin, elongate primary tube 702 with a closed wall 704, open proximal end 706, and opposite open distal end 708. First and second internal tubes, respectively 710a and 710b, extend from the distal end 708 of the primary tube 702, with the first and second internal tubes each comprising a long, thin element having a wall, respectively 712a and 712b, an open proximal end, respectively 714a and 714b, and opposite open distal end, respectively 716a and 716b. The proximal ends 714a, 714b of the two internal tubes 710a, 710b are joined to and communicate with the distal end 708 of the primary tube 702 and with one another and form a small acute angle 718 between the two proximal ends 714a, 714b, e.g., on the order of twenty to thirty degrees included angle therebetween. The walls 712a, 712b of the two internal tubes 710a, 710b have closed portions 720a, 720b extending for some lengths from points adjacent their proximal ends 714a, 714b, but have porous portions 722a, 722b extending for some lengths from points adjacent their distal ends 716a, 716b to the closed wall portions 720a, 720b thereof. The bifurcated peritoneal catheter 700 of FIG. 7 includes two annular cuffs thereon, as in the catheter embodiments 300 through 600, respectively of FIGS. 3 through 6. A first annular cuff 724 comprising a subcutaneous cuff is located about the medial portion 726 of the primary tube 702, with a second or deep cuff 728 disposed about the distal end 708 of the primary tube 702 adjacent its juncture with the proximal ends 714a and 714b of the two internal tubes 710a and 710b.

The bifurcated peritoneal catheter embodiment 700 of FIG. 7 differs from the embodiment 600 of FIG. 6 due to the curvature or coil of the second internal tube 610b. In the example of FIG. 7, the coiled portion 722b of the second internal tube 710b is coiled in a second direction, e.g., clockwise in the plan view of FIG. 7, resulting in its coil being away the straight length of the first internal tube 710a.

Figure 8:
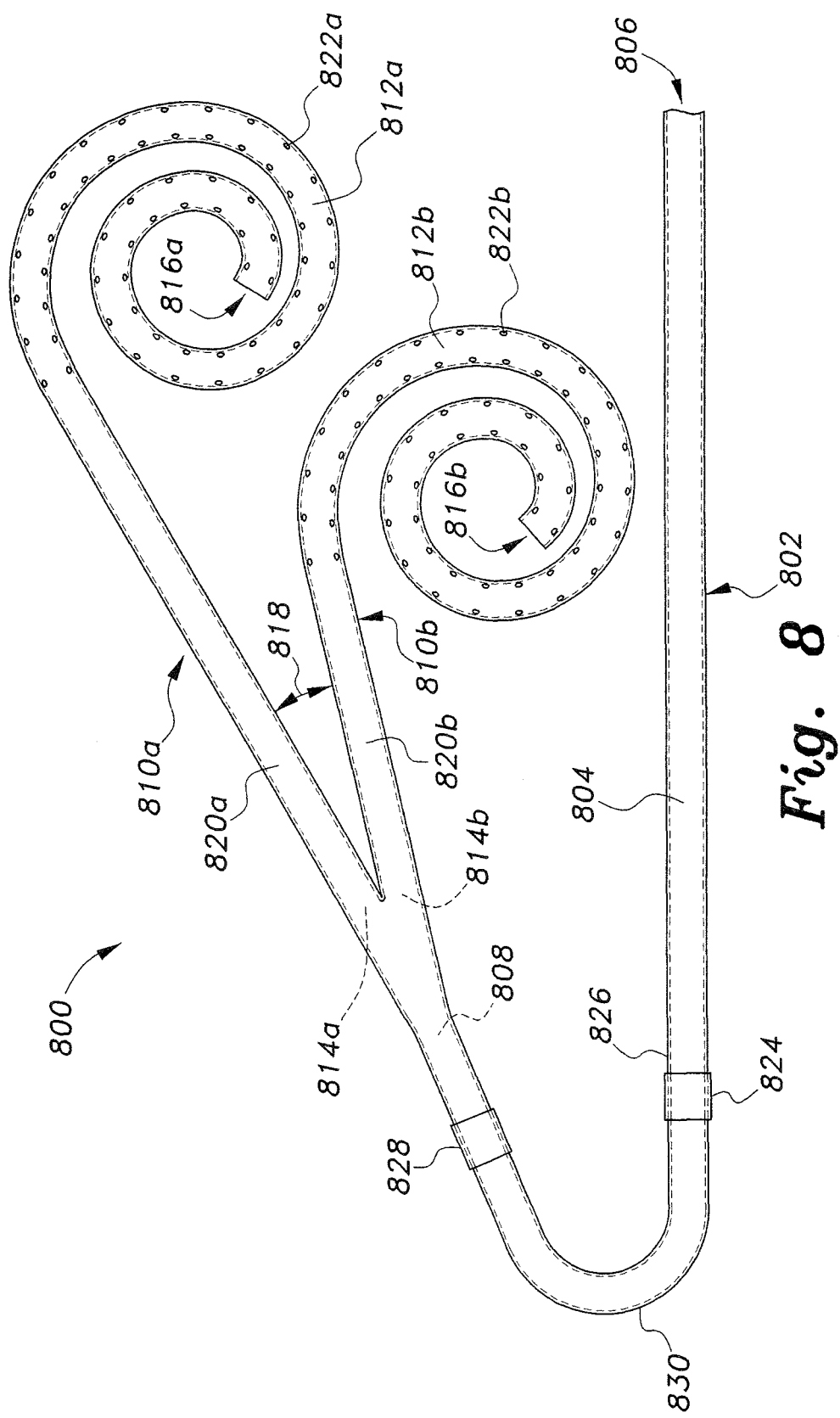
FIG. 8 is a top plan view of an eighth embodiment of the bifurcated peritoneal catheter according to the present invention, wherein the entry tube includes an acute bend between the two cuffs and the two peritoneal tubes are coiled toward the entry tube.

FIG. 8 of the drawings illustrates an eighth embodiment 800 of the bifurcated peritoneal catheter. The components of the catheter 800 are quite similar to those of the catheter 500 of FIG. 5, i.e., having a thin, elongate primary tube 802 with a closed wall 804, open proximal end 806, and opposite open distal end 808. First and second internal tubes, respectively 810a and 810b, extend from the distal end 808 of the primary tube 802, with the first and second internal tubes each comprising a long, thin element having a wall, respectively 812a and 812b, an open proximal end, respectively 814a and 814b, and opposite open distal end, respectively 816a and 816b. The proximal ends 814a, 814b of the two internal tubes 810a, 810b are joined to and communicate with the distal end 808 of the primary tube 802 and with one another and form a small acute angle 818 between the two proximal ends 814a, 814b, e.g., on the order of twenty to thirty degrees included angle therebetween. The walls 812a, 812b of the two internal tubes 810a, 810b have closed portions 820a, 820b extending for some lengths from points adjacent their proximal ends 814a, 814b, but have porous portions 822a, 822b extending for some lengths from points adjacent their distal ends 816a, 816b to the closed wall portions 820a, 820b thereof. The bifurcated peritoneal catheter 800 of FIG. 8 includes two annular cuffs thereon, as in the catheter embodiments 300 through 700 respectively of FIGS. 3 through 7. A first annular cuff 824 comprising a subcutaneous cuff is located about the medial portion 826 of the primary tube 802, with a second or deep cuff 828 disposed about the distal end 808 of the primary tube 802 adjacent its juncture with the proximal ends 814a and 814b of the two internal tubes 810a and 810b.

The bifurcated peritoneal catheter embodiment 800 of FIG. 8 differs from the embodiment 500 of FIG. 5 due to the orientation of the coiled porous portion 822a of the first internal tube 810a. In FIG. 8, the coiled porous portion 822a of the first internal tube 810a is coiled in the same orientation or direction as the coiled porous portion 822b of the second internal tube 810b, i.e., both are coiled in a first or clockwise orientation as viewed from the orientation shown in FIG. 8.

Figure 9:
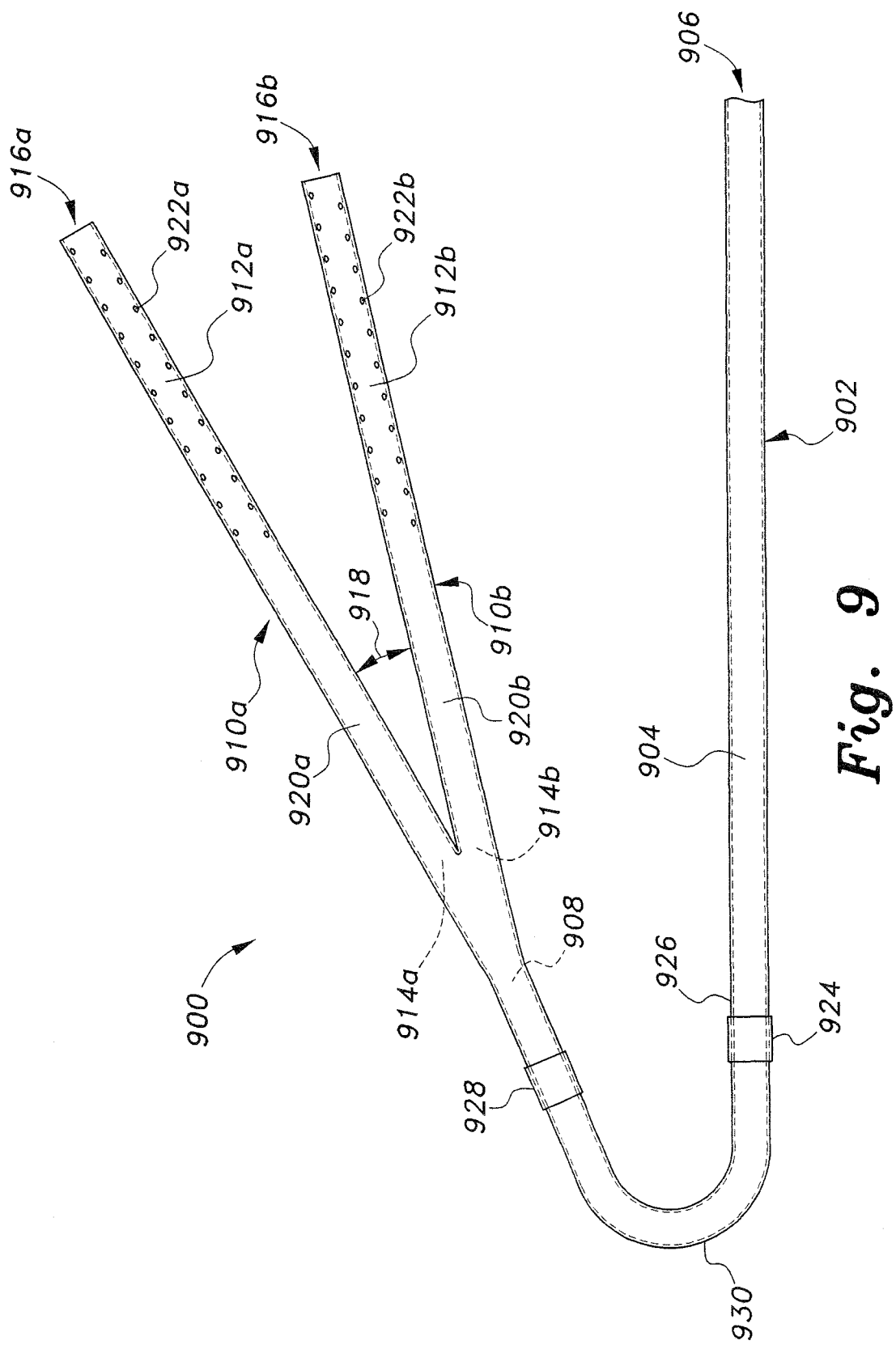
FIG. 9 is a top plan view of a ninth embodiment of the bifurcated peritoneal catheter according to the present invention, wherein the entry tube includes an acute bend between the two cuffs and the two peritoneal tubes are straight.

FIG. 9 of the drawings illustrates a ninth embodiment 900 of the bifurcated peritoneal catheter. The components of the catheter 900 are somewhat analogous to those of the catheter 500 of FIG. 5, but rather than the internal tubes of the catheter being coiled as in the catheter embodiment 500 of FIG. 5, the internal tubes of the catheter embodiment 900 of FIG. 9 are straight. The catheter 900 has a thin, elongate primary tube 902 with a closed wall 904, open proximal end 906, and opposite open distal end 908. First and second internal tubes, respectively 910a and 910b, extend from the distal end 908 of the primary tube 902, with the first and second internal tubes each comprising a long, thin element having a wall, respectively 912a and 912b, an open proximal end, respectively 914a and 914b, and opposite open distal end, respectively 916a and 916b. The proximal ends 914a, 914b of the two internal tubes 910a, 910b are joined to and communicate with the distal end 908 of the primary tube 902 and with one another and form a small acute angle 918 between the two proximal ends 914a, 914b, e.g., on the order of twenty to thirty degrees included angle therebetween. The walls 912a, 912b of the two internal tubes 910a, 910b have closed portions 920a, 920b extending for some lengths from points adjacent their proximal ends 914a, 914b, but have porous portions 922a, 922b extending for some lengths from points adjacent their distal ends 916a, 916b to the closed wall portions 920a, 920b thereof. The bifurcated peritoneal catheter 900 of FIG. 9 includes two annular cuffs thereon, as in the catheter embodiments 300 through 800 respectively of FIGS. 3 through 8. A first annular cuff 924 comprising a subcutaneous cuff is located about the medial portion 926 of the primary tube 902, with a second or deep cuff 928 disposed about the distal end 908 of the primary tube 902 adjacent its juncture with the proximal ends 914a and 914b of the two internal tubes 910a and 910b.

The bifurcated peritoneal catheter embodiment 900 of FIG. 9 differs from the embodiment 800 of FIG. 8 in that the two internal tubes 810a and 810b are both straight, and diverge from their juncture with the distal end 808 of the primary tube 802 by a constant small included angle, as described further above. Otherwise, the bifurcated peritoneal catheter 900 of FIG. 9 is substantially the same as the bifurcated peritoneal catheter of FIG. 8.

Figure 10:
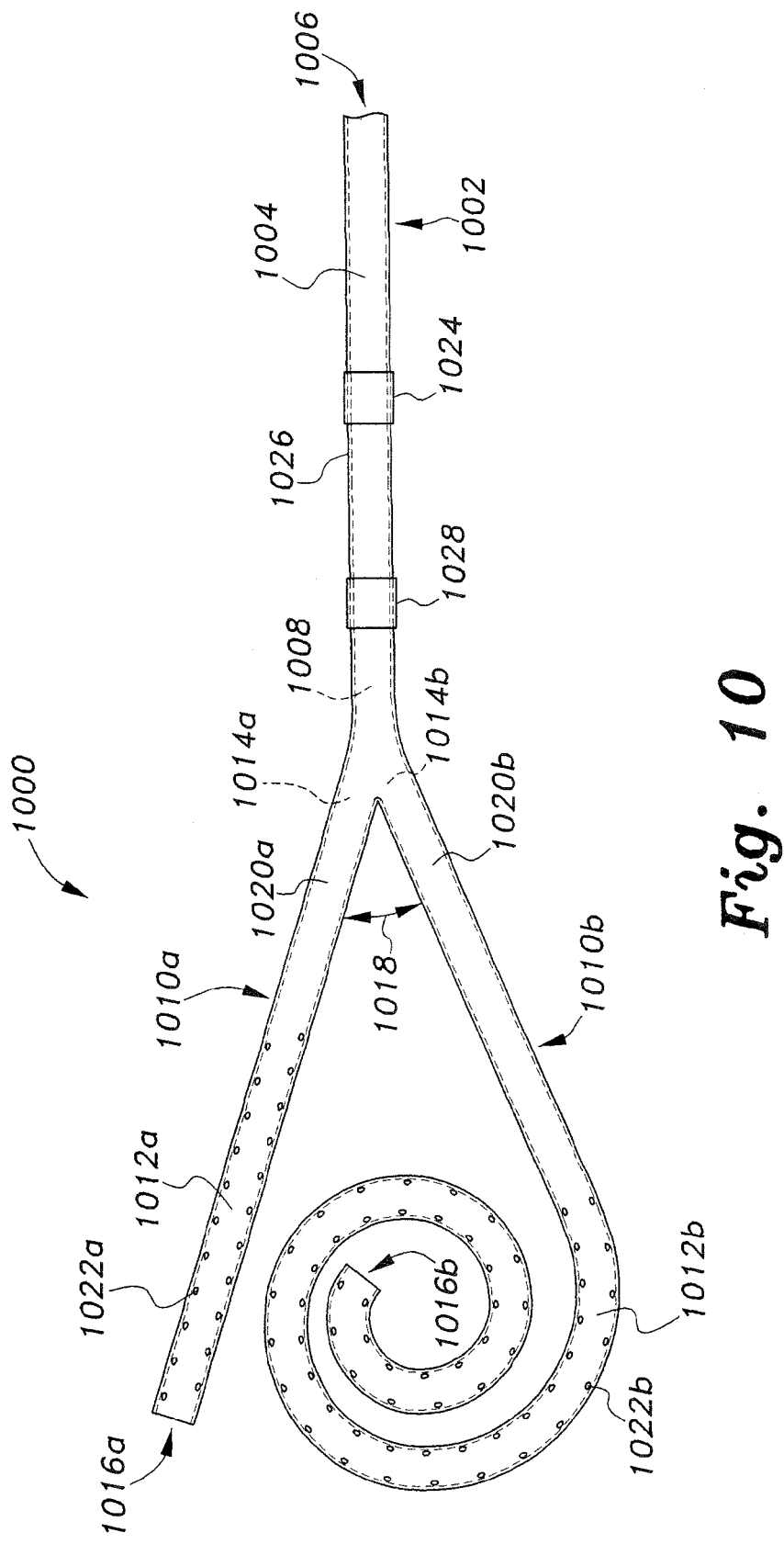
FIG. 10 is a top plan view of a tenth embodiment of the bifurcated peritoneal catheter according to the present invention, wherein the entry tube is straight between the two cuffs and one of the two peritoneal tubes is coiled toward the other.

FIG. 10 of the drawings illustrates a tenth embodiment 1000 of the bifurcated peritoneal catheter. The catheter 1000 is essentially a combination of the catheter 400 of FIG. 4 with its straight primary tube and the catheter 600 of FIG. 6 with its coiled perforated portion of the second internal tube. The catheter 1000 has a thin, elongate primary tube 1002 with a closed wall 1004, open proximal end 1006, and opposite open distal end 1008. First and second internal tubes, respectively 1010a and 1010b, extend from the distal end 1008 of the primary tube 1002, with the first and second internal tubes each comprising a long, thin element having a wall, respectively 1012a and 1012b, an open proximal end, respectively 1014a and 1014b, and opposite open distal end, respectively 1016a and 1016b. The proximal ends 1014a, 1014b of the two internal tubes 1010a, 1010b are joined to and communicate with the distal end 1008 of the primary tube 1002 and with one another and form a small acute angle 1018 between the two proximal ends 1014a, 1014b, e.g., on the order of twenty to thirty degrees included angle therebetween. The walls 1012a, 1012b of the two internal tubes 1010a, 1010b have closed portions 1020a, 1020b extending for some lengths from points adjacent their proximal ends 1014a, 1014b, but have porous portions 1022a, 1022b extending for some lengths from points adjacent their distal ends 1016a, 1016b to the closed wall portions 1020a, 1020b thereof.

The bifurcated peritoneal catheter embodiment 1000 of FIG. 10 differs from the embodiment 400 of FIG. 4 in that the first internal tube 1010a is straight, while the porous portion 1022b of the second internal tube 1010b is coiled toward the first internal tube 1010a. This configuration of the internal tubes is similar to that of the sixth embodiment catheter 600 of FIG. 6. However, the catheter 1000 of FIG. 10 is similar to the embodiments 300 of FIG. 3 and 400 of FIG. 4 in that the primary tube 1002 is straight, rather than having an acute bend or curve therein. It will also be seen that the bifurcated peritoneal catheter 1000 of FIG. 4 includes two annular cuffs thereon, as in the embodiments 300 and 400 respectively of FIGS. 3 and 4. A first annular cuff 1024 comprising a subcutaneous cuff is located about the medial portion 1026 of the primary tube 1002, with a second or deep cuff 1028 disposed about the distal end 1008 of the primary tube 1002 adjacent its juncture with the proximal ends 1014a and 1014b of the two internal tubes 1010a and 1010b.

Figure 11:
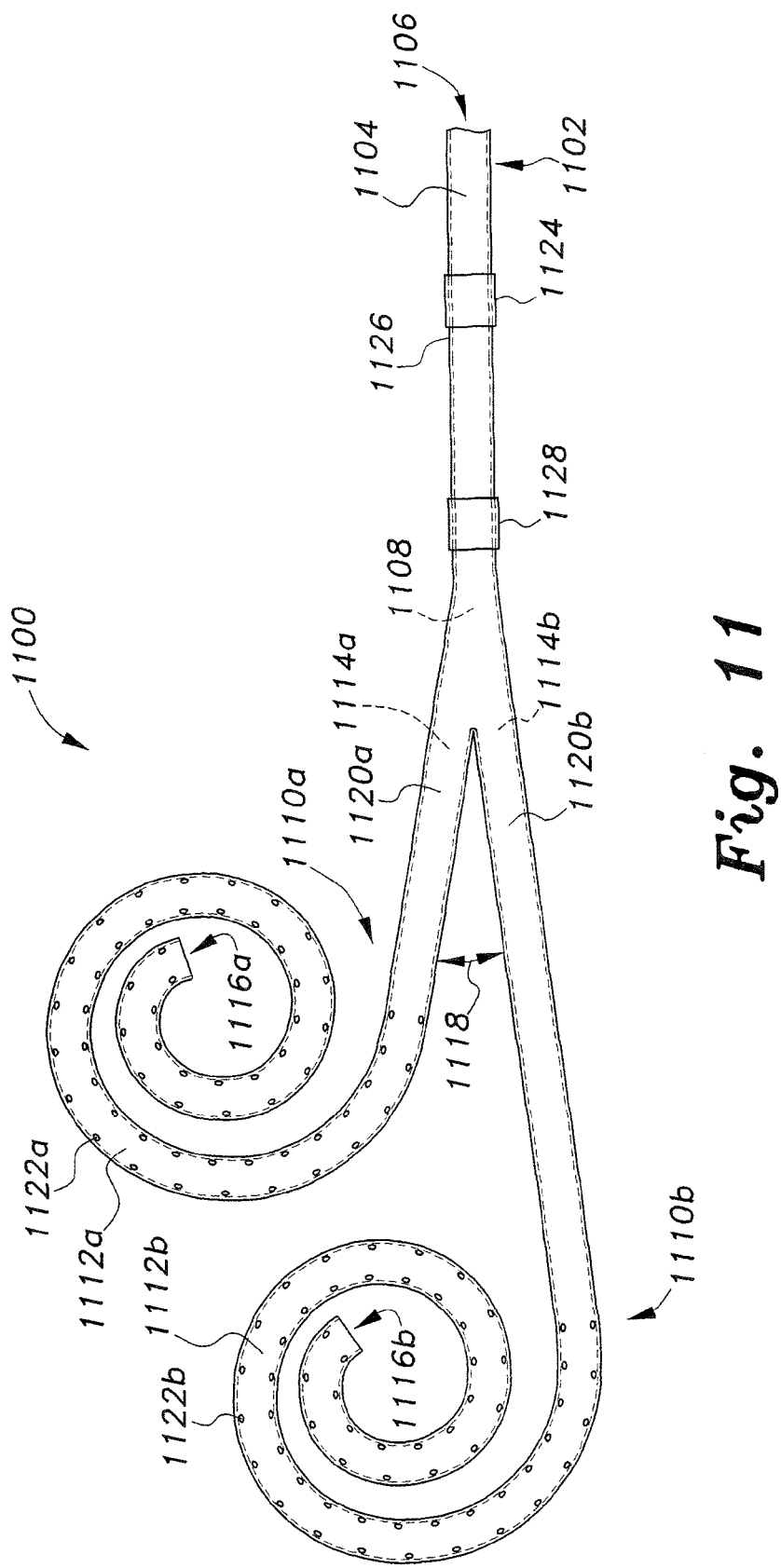
FIG. 11 is a top plan view of an eleventh embodiment of the bifurcated peritoneal catheter according to the present invention, wherein the entry tube is straight between the two cuffs and the two peritoneal tubes are coiled in the same direction.

FIG. 11 of the drawings illustrates an eleventh embodiment 1100 of the bifurcated peritoneal catheter. The catheter 1100 is essentially a combination of the catheter 400 of FIG. 4 with its straight primary tube and the catheter 800 of FIG. 8 with its two coiled perforated portions of its two internal tubes. The catheter 1100 has a thin, elongate primary tube 1102 with a closed wall 1104, open proximal end 1106, and opposite open distal end 1108. First and second internal tubes, respectively 1110a and 1110b, extend from the distal end 1108 of the primary tube 1102, with the first and second internal tubes each comprising a long, thin element having a wall, respectively 1112a and 1112b, an open proximal end, respectively 1114a and 1114b, and opposite open distal end, respectively 1116a and 1116b. The proximal ends 1114a, 1114b of the two internal tubes 1110a, 1110b are joined to and communicate with the distal end 1108 of the primary tube 1102 and with one another and form a small acute angle 1118 between the two proximal ends 1114a, 1114b, e.g., on the order of twenty to thirty degrees included angle therebetween. The walls 1112a, 1112b of the two internal tubes 1110a, 1110b have closed portions 1120a, 1120b extending for some lengths from points adjacent their proximal ends 1114a, 1114b, but have porous portions 1122a, 1122b extending for some lengths from points adjacent their distal ends 1116a, 1116b to the closed wall portions 1120a, 1120b thereof. A first annular cuff 1124 comprising a subcutaneous cuff is located about the medial portion 1126 of the primary tube 1102, with a second or deep cuff 1128 disposed about the distal end 1108 of the primary tube 1102 adjacent its juncture with the proximal ends 1114a and 1114b of the two internal tubes 1110a and 1110b.

The bifurcated peritoneal catheter embodiment 1100 of FIG. 11 differs from the embodiment 800 of FIG. 8 in that the primary tube 1102 is straight, rather than having an acute bend or curve therein. The two perforated portions 1122a and 1122b of the internal tubes 1110a and 1110b are both coiled in the same direction, i.e., clockwise. This is the same orientation as the coils of the perforated portions 822a, 822b of the catheter embodiment 800 of FIG. 8, but the orientation may appear different in the embodiment 1100 of FIG. 11 due to the straight primary tube 1102.

Figure 12:
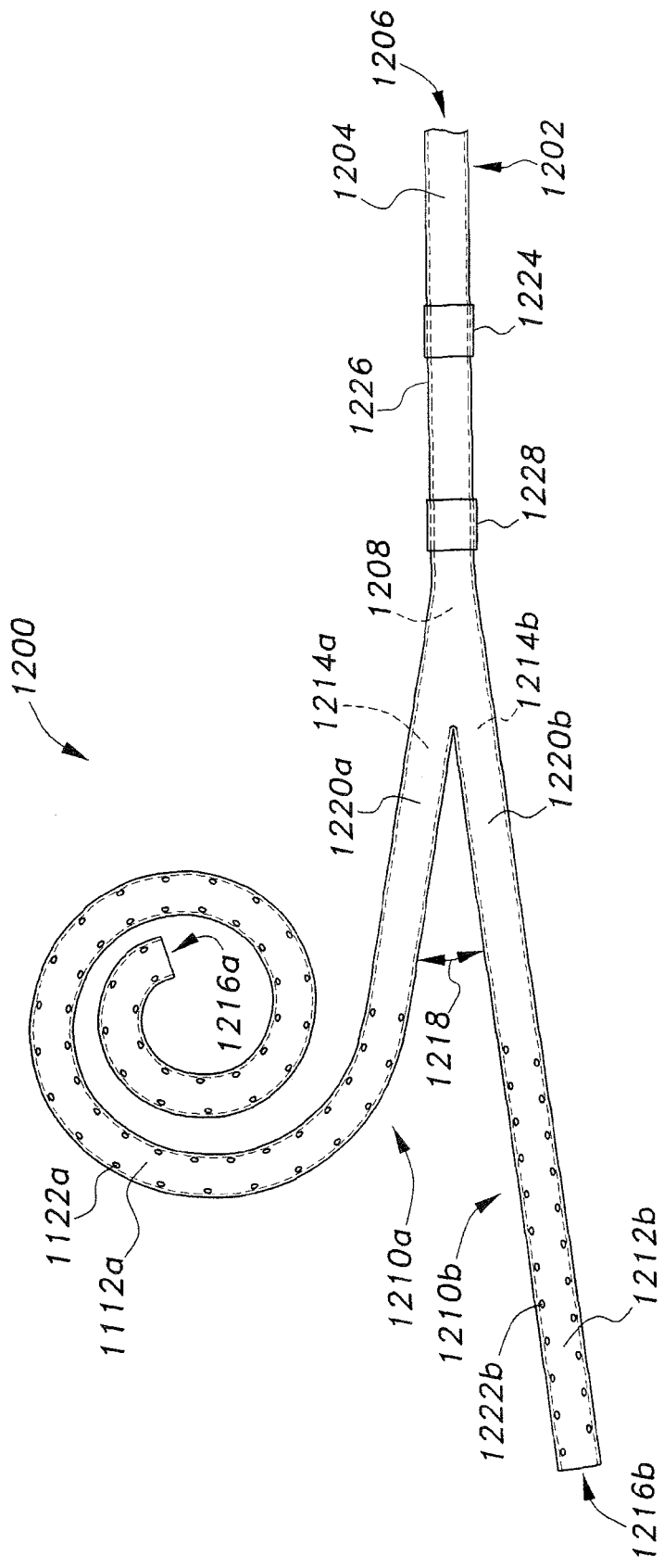
FIG. 12 is a top plan view of a twelfth embodiment of the bifurcated peritoneal catheter according to the present invention, wherein the entry tube is straight between the two cuffs and one of the peritoneal tubes are coiled away from the other.

FIG. 12 of the drawings illustrates a twelfth embodiment 1200 of the bifurcated peritoneal catheter. The catheter 1200 most closely resembles the catheter 1000 of FIG. 10, excepting the relative placement of the straight and curved internal tubes. The catheter 1200 has a thin, elongate primary tube 1202 with a closed wall 1204, open proximal end 1206, and opposite open distal end 1208. First and second internal tubes, respectively 1210a and 1210b, extend from the distal end 1208 of the primary tube 1202, with the first and second internal tubes each comprising a long, thin element having a wall, respectively 1212a and 1212b, an open proximal end, respectively 1214a and 1214b, and opposite open distal end, respectively 1216a and 1216b. The proximal ends 1214a, 1214b of the two internal tubes 1210a, 1210b are joined to and communicate with the distal end 1208 of the primary tube 1202 and with one another and form a small acute angle 1218 between the two proximal ends 1214a, 1214b, e.g., on the order of twenty to thirty degrees included angle therebetween. The walls 1212a, 1212b of the two internal tubes 1210a, 1210b have closed portions 1220a, 1220b extending for some lengths from points adjacent their proximal ends 1214a, 1214b, but have porous portions 1222a, 1222b extending for some lengths from points adjacent their distal ends 1216a, 1216b to the closed wall portions 1220a, 1220b thereof. A first annular cuff 1224 comprising a subcutaneous cuff is located about the medial portion 1226 of the primary tube 1202, with a second or deep cuff 1228 disposed about the distal end 1208 of the primary tube 1202 adjacent its juncture with the proximal ends 1214a and 1214b of the two internal tubes 1210a and 1210b.

The bifurcated peritoneal catheter embodiment 1200 of FIG. 12 differs from the embodiment 1000 of FIG. 10 in that the porous portion 1222a of the first internal tube 1210a is coiled, while the second internal tube 1210b is straight. The orientation of the porous coiled portions 1022b of the embodiment of FIGS. 10 and 1222a of the embodiment of FIG. 12 is the same, i.e., clockwise in both cases. It will be seen that this orients the coil of the second internal tube 1010b of the embodiment of FIG. 10 toward the opposite first internal tube 1010a, while the coil of the first internal tube 1210a of the embodiment of FIG. 12 is oriented away from the opposite second internal tube 1210b.

Figure 13:
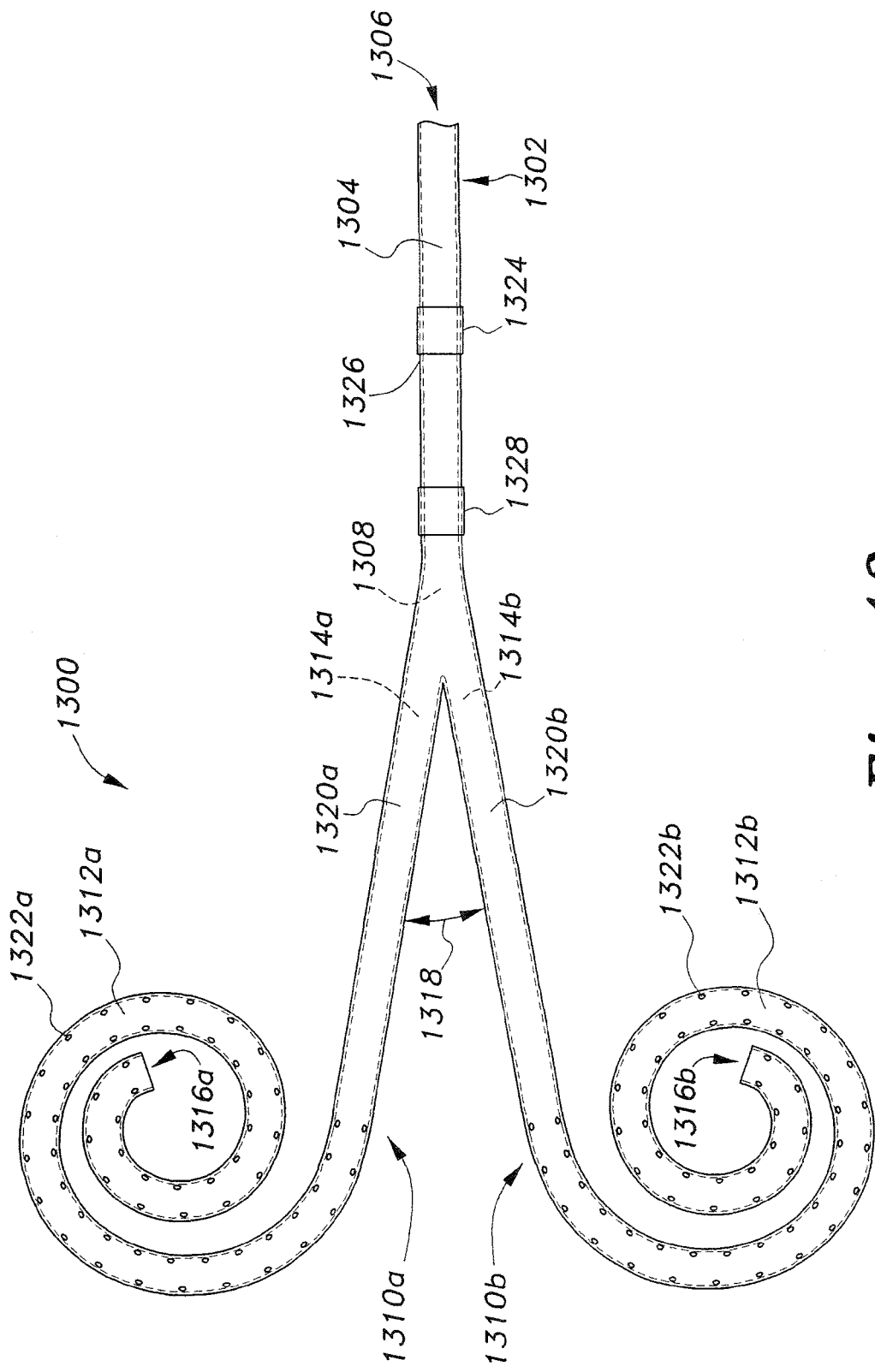
FIG. 13 is a top plan view of a thirteenth embodiment of the bifurcated peritoneal catheter according to the present invention, wherein the entry tube is straight between the two cuffs and the two peritoneal tubes are coiled away from each other.

FIG. 13 of the drawings illustrates a thirteenth embodiment 1300 of the bifurcated peritoneal catheter. The catheter 1300 is similar to the catheter 1100 of FIG. 11, excepting the orientation of the porous coiled portion of the second internal tube. The catheter 1300 has a thin, elongate primary tube 1302 with a closed wall 1304, open proximal end 1306, and opposite open distal end 1308. First and second internal tubes, respectively 1310a and 1310b, extend from the distal end 1308 of the primary tube 1302, with the first and second internal tubes each comprising a long, thin element having a wall, respectively 1312a and 1312b, an open proximal end, respectively 1314a and 1314b, and opposite open distal end, respectively 1316a and 1316b. The proximal ends 1314a, 1314b of the two internal tubes 1310a, 1310b are joined to and communicate with the distal end 1308 of the primary tube 1302 and with one another and form a small acute angle 1318 between the two proximal ends 1314a, 1314b, e.g., on the order of twenty to thirty degrees included angle therebetween. The walls 1312a, 1312b of the two internal tubes 1310a, 1310b have closed portions 1320a, 1320b extending for some lengths from points adjacent their proximal ends 1314a, 1314b, but have porous portions 1322a, 1322b extending for some lengths from points adjacent their distal ends 1316a, 1316b to the closed wall portions 1320a, 1320b thereof. A first annular cuff 1324 comprising a subcutaneous cuff is located about the medial portion 1326 of the primary tube 1302, with a second or deep cuff 1328 disposed about the distal end 1308 of the primary tube 1302 adjacent its juncture with the proximal ends 1314a and 1314b of the two internal tubes 1310a and 1310b.

The bifurcated peritoneal catheter embodiment 1300 of FIG. 13 differs from the embodiment 1100 of FIG. 11 in that the porous coiled portion 1322b of the second internal tube 1310b is coiled in the opposite direction from the corresponding portion 1322a of the first internal tube 1310a, i.e., counterclockwise, with the coiled porous portion 1322a of the first internal tube being coiled clockwise. In other words, the first and second internal tubes 1310a, 1310b are coiled away from one another.

It will be seen that further permutations and combinations of the bidirectional peritoneal catheter can be provided in addition to those illustrated in the drawing Figs. and described above. Such permutations and combinations can include one or two cuffs, straight or curved primary tubes, various combinations of straight and curved or coiled internal tubes, etc., as desired.

It is to be understood that the present invention is not limited to the embodiments described above, but encompasses any and all embodiments within the scope of the following claims.

I claim:

1. A bifurcated peritoneal catheter, comprising:
   an elongate, primary tube having a closed wall with an open proximal end and an open distal end opposite the proximal end, wherein the distal and proximal ends are separated by a swan-neck curve portion;
   a first internal tube and a second internal tube, each internal tube comprising an element having a wall with an open proximal end and an open distal end opposite the proximal end, the proximal ends of the internal tubes being directly connected to and communicating directly with the distal end of the primary tube, the proximal ends of the internal tubes being joined to and communicating with one another and defining an acute angle of between 20-30 degrees, wherein the first internal tube is coiled in a first direction and the second internal tube is coiled in a second direction opposite the first direction of the first internal tube, wherein each of the coiled portions subtending approximately 570 degrees, the walls of the internal tubes further having closed portions adjacent the proximal ends thereof and porous portions adjacent the distal ends thereof, the primary tube and the internal tubes being adapted for simultaneous unidirectional flow therethrough;
   a first annular cuff disposed concentrically about the primary tube on the distal portion of the swan-neck curve portion, wherein the cuff is spaced proximally from the connection of the proximal ends of the first and second internal tubes to the primary tube; and
   a second annular cuff disposed concentrically about the primary tube on the proximal portion of the swan-neck curve portion.

* * * * *